United States Patent
Riede et al.

Patent Number: 5,360,915
Date of Patent: Nov. 1, 1994

[54] MODIFIED HUMINATES AND THEIR PREPARATION

[75] Inventors: Urs N. Riede, Frieburg; Bernhard Seubert, Edingen, both of Germany

[73] Assignee: Rutgerswerke Aktiengesellschaft AG, Germany

[21] Appl. No.: 960,895

[22] Filed: Oct. 14, 1992

[30] Foreign Application Priority Data

Oct. 17, 1991 [DE] Germany .................. 4134384

[51] Int. Cl.$^5$ .................. C07D 493/22; C07D 521/00; C07D 519/00; C08G 83/00
[52] U.S. Cl. .................. 549/200; 549/348; 549/354; 549/399; 549/400; 549/406
[58] Field of Search .............. 514/456, 450; 549/399, 549/400, 406, 200, 348, 354

[56] References Cited

U.S. PATENT DOCUMENTS

| | | | |
|---|---|---|---|
| 3,450,717 | 6/1969 | Kraemer et al. | 549/400 X |
| 3,598,840 | 8/1971 | Majoie | 549/400 |
| 4,942,181 | 7/1990 | Riede et al. | 514/730 |

OTHER PUBLICATIONS

Hackh's Chemical Dictionary, 4th ed., 1975, p. 328.
Pang et al, Advances in Organic Geochemistry, 1990, pp. 853-864.
Tzouwara-Karayanni et al., Mikrochimica Acta, 1983, II, pp. 151-157.
Marchesini et al., Analytical Chemistry Symposia Series, vol. 14, Chromatography and Mass Spectrometry in Biomedical Sciences, 2, 1982, pp. 149-157.

*Primary Examiner*—Johann Richter
*Assistant Examiner*—Michael B. Hydorn
*Attorney, Agent, or Firm*—Bierman and Muserlian

[57] ABSTRACT

A modified alkali metal or ammonium huminate being made from molecules of the group consisting of

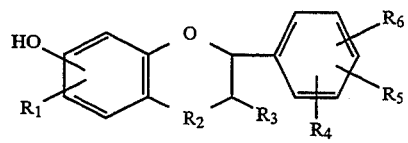

and

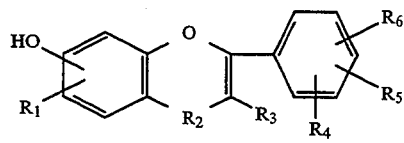

wherein $R_1$, $R_3$ and $R_4$ are individually hydrogen or —OH, $R_2$ is

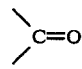

or —CH$_2$— and $R_5$ and $R_6$ are individually selected from the group consisting of hydrogen, —OH and —OCH$_3$, with the proviso that $R_4$, $R_5$ and $R_6$ are not all hydrogen at the same time and their preparation and their medical uses.

2 Claims, No Drawings

MODIFIED HUMINATES AND THEIR PREPARATION

STATE OF THE ART

European Patent application No. A 0,281,678 describes a process for the synthetic production of low molecular weight alkali metal huminates by oxidation of polyvalent phenols in a weakly alkaline medium which huminates have low toxicity but a wound healing and detoxicating activity over a wide-range as taught in U.S. Pat. No. 4,942,840; DEA 3,830,616; DEA 4,022,795; P 41 05 395.8 and P 41 20 396.7. However, the specific efficacy is relatively slight.

OBJECTS OF THE INVENTION

It is an object of the invention to provide novel alkali metal or ammonium huminates with low toxicity and a higher specific efficacy with a broad range of activity and a process for their preparation.

It is another object of the invention to provide novel therapeutic compositions and methods with low toxicity.

These and other objects and advantages will become obvious from the following detailed description.

THE INVENTION

The modified alkali metal and ammonium huminates of the invention are those being at least partially made from molecules of the group consisting of

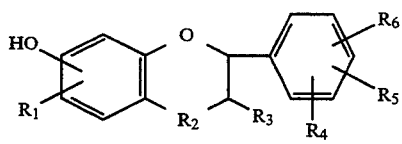

and/or

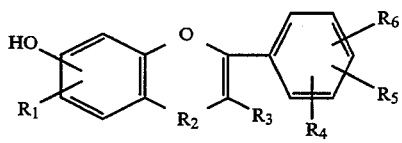

wherein $R_1$, $R_3$ and $R_4$ are individually hydrogen or —OH, $R_2$ is

or —$CH_2$— and $R_5$ and $R_6$ are individually selected from the group consisting of hydrogen, —OH and —$OCH_3$, with the proviso that $R_4$, $R_5$ and $R_6$ are not all hydrogen at the same tame.

The modified alkali metal and ammonium huminates are not toxic and have the same broad spectrum of activity as the natural huminates described in European Patent No. 0,281,679 and the synthetic low molecular weight huminates described in European Patent No. 0,281,676. However, the modified huminates of the invention are up to 100 times more effective than the unmodified low-molecular weight alkali metal huminates.

The modified alkali metal or ammonium huminates are composed either exclusively or partially of molecules of formulas I and/or II with the possible other building blocks being polyvalent phenols.

Examples of molecules of the formulae I or II are narigenin, eriodictyol, resperitin, pelargonidin, delphinidin, peonidin, syringidin, catechin or epicatechin, gallocatechin, apigenin, fisetin, robinetin, gossypetin, luteolin, camphorol, quercetin, morin and myricetin. Preferred building blocks are quercetin and catechin.

The modified alkali metal or ammonium huminates are produced by oxidizing aqueous alkaline solutions with a pH>9 which contain compounds of the formulae I and/or II at a temperature in the range of 15° to 40° C. and then the reaction mixture is adjusted and/or buffered to a pH value in the neutral or weakly acid range of 4.5 to 7, preferably 5.5 to 6.5 and the huminates are purified and separated from undesired by products by preparative chromatography methods, ultrafiltration, ultracentrifugation or electrodialysis.

The compounds of formulae I and II can be used as pure substances and also in any mixture with one another. They can also be used in the reaction mixture with polyvalent phenols which for economic reasons may be quite appropriate. As the resulting modified huminates of compounds of formulae I and/or II and of polyvalent phenols show diminished physiological efficacy with increasing proportion of polyvalent phenols, the preferred molar ratio of the compounds of the formulae I and/or II to polyvalent phenols is in the range of 1:0 to 1:10.

Naturally, the compounds used should be as free as possible from other by products, for thereby undesired secondary reactions are avoided or respectively the end products can be obtained without further chemical processing which too would be connected with undesired chemical alterations of the end products.

For the reaction, the compounds of formulae I and/or II as well as possibly the polyvalent phenols are dissolved in an aqueous alkali metal hydroxide or ammonium hydroxide solution. The alkali metal hydroxides include all alkali metal hydroxides, but for economic reasons, sodium hydroxide and potassium hydroxide are preferred. The amount of ammonium hydroxide or alkali metal hydroxide used is preferably in the range of 1.8 to 2.0 times the stoichiometric quantity needed to neutralize all phenolic OH groups. A pH value of the reaction solution of 9 to 12 then adjusts itself. However, even a higher pH value up to about 14 is not disturbing.

Generally, it suffices to use as water demineralized water with a conductivity of 6 to 10/μS/cm and a pH value in the range of 5 to 7. The alkali metal hydroxide is either "chemically pure" grade or the purity per DAB 9.

The oxidation of the products used in alkaline solution can take place either electrochemically or plasmachemically or respectively chemically by conducting oxygen or an oxygen-containing gas mixture through or over it. The electrochemical oxidation occurs in an electrochemical reactor with the rate of oxidation being determined by setting the anodic voltage and the current density. The anodic voltage can be varied in the range from 4 to 15 volts and the current density is in the range from 0.5 to 4 A/cm². The reaction time is then in the range of 1 to 3 days.

The plasmachemical oxidation occurs in an apparatus known per se for corona discharge with the oxidation rate being determined by the operating voltage and the field strength. The voltage may be varied in the range of 20 to 250 kV at frequencies of 16⅔ to 400 Hz and the field strength of 80 kV/cm to 200 kV/cm with the reaction time being in the range of 15 to 120 minutes.

For the chemical oxidation, the alkaline solution of the compounds of Formulae I and/or II is placed in a reaction vessel which prevents uncontrolled access of air, that is, in a closed reaction vessel provided with a device for letting gases in or through. While stirring, oxygen or an oxygen-containing gas mixture is passed in a continuous gas stream either over or through the reaction solution or is conducted under pressure onto the reaction solution with the temperature of the reaction mixture being in the range of 10° to 40° C., preferably in the range from room temperature to 30° C. The oxygen-containing gas mixture can be air, which, however, must first be conducted over an alkaline filter for the adsorption of $CO_2$ and for the removal of dust particles. This oxidation reaction takes 5 to 20 days, depending on the selected temperature and intensity of the oxygen supply. During the reaction time, the solution takes on an intensive dark brown color. The chemical oxidation can also occur by reaction with mild oxidants such as hydrogen peroxide, its addition compounds, or persulfates.

It is an advantage of the process of the invention that, when using compounds of formulae I and/or II in weakly alkaline medium, both with the electrochemical oxidation and with the plasmachemical and the chemical oxidation, the reaction of formation of the modified huminates does not lead to high-molecular weight products, but automatically stops at products with a molecular weight of up to 30,000 D. This makes continual control of the progress of the oxidation reaction unnecessary, and it is not disadvantageous if the reaction time is longer than would be necessary.

The dark brown solution resulting from the chemical, plasmachemical, or electrochemical oxidation reaction is neutralized and adjusted and buffered to a pH value in the range of 4.5 to 7.0, preferably 5.5 to 6.5. This is done either by addition of acid or by action of an acid ion exchanger and/or subsequent addition of an appropriate buffer solution e.g. phosphate, tris or citric acid buffer.

If the neutralized and buffered solution contains undesired suspended substances, these are removed therefrom by separating methods such as centrifuging at 10,000 to 30,000 xg or filtering through a very fine-pore filter material. Although for many applications this solution can be used directly, it should be purified by purification processes known in themselves such as preparative chromatography methods, ultrafiltration, ultracentrifugation or electrodialysis and liberated from undesired by-products for use of the products in medicaments.

The resulting solution contains about 3 to 5% modified huminates with a molecular weight up to 30,000 D. The solution shows no Tyndall effect and does not fluoresce and this solution can be used directly or concentrated to a 20% solution by careful removal of water, for instance by freeze drying. The solution obtained is stable as is the concentrated solution.

In stability tests, after 60 days of load cycles at 56/4° C. in a 12/12 hour rhythm, no alteration of the parameters content, pH value, redox potential and microdialysis test beyond the incidental fluctuations is observable. The modified huminates show an extremely low toxicity, but high physiological and detoxicating activity. Thus, for example, the wound healing action is up to one hundred times greater than that of the natural and synthetic huminates.

The modified low-molecular weight huminates of the invention are therefore suitable for all applications that are known of the natural or synthetic low-molecular weight huminates. They are particularly suitable for use as vulnerary, for the preparation of wound healing agents, for the preparation of highly effective moor baths, of nose sprays against pollen allergies, of antidandruff shampoos as well as of agents for the treatment of fish, particularly stressed fish. Moreover, the modified huminates are suitable for detoxicating water as well as surfaces or solid objects.

In the following examples, there are described several preferred embodiments to illustrate the invention. However, it is to be understood that the invention is not intended to be limited to the specific embodiments.

EXAMPLE 1

29 g (0.1 mole) of catechin [2-(3,4-dihydroxyphenyl)-chromane-3,5,7-triol] were dissolved at room temperature in 1,000 ml of an aqueous 0.8 molar sodium hydroxide solution. The solution with a pH 10 was placed in a glass reactor equipped with a stirrer, a thermometer, a gas inlet and a pressure relief device. Then, air previously purified by removal of $CO_2$ and dust particles with a sodium hydroxide solution in a gas washing bottle was passed through the solution at room temperature in a continuous gas stream. The gas stream was regulated so that the temperature of the reaction solution was maintained at 30° C. After a reaction time of 10 days, when despite further air supply, the temperature of the reaction solution dropped, the reaction was ended. The resulting dark brown solution was adjusted to a pH of 6.0 by the addition of dilute acetic acid and was then purified by ultrafiltration. The purified solution contained 4.2% of a modified huminate with a mean molecular weight of 2,500 D with a range of 1,000 to 30,000 D. The solution was dark brown, did not fluoresce, and showed no Tyndall effect.

EXAMPLE 2

Superficial wounds affecting only the topmost epithelium layers were inflicted in a size of about 50 mm², using a microdermatome on 2×10 hairless mice. In ten of these mice, the wound was wetted once with a 0.02% solution of the modified huminate of Example 1 and the other mice remained untreated. During an observation time of 7 days, the following was observed: As compared with the untreated mice, in the treated test animals the wound area decreased faster, the wound dried up earlier, the granulation set in earlier, and the wound became clean earlier. On the whole, the healing was observable 2 to 3 days earlier than in the control animals.

EXAMPLE 3

A culture of L-cells (mouse fibroblasts) suspended after thrypsin treatment was mixed with 5 ppm of the modified huminate of Example 1 and the culture was incubated at 37° C. for 48 hours using a commerical culture medium. At the same time, an analogous culture without alkali metal huminate was incubated in the same manner as a comparison test. Then, the number of living cells was determined in both cultures. In the culture mixed with modified huminates, the number of living cells was 40% higher than in the comparison culture.

EXAMPLE 4

With injections of a 1% solution of the modified huminate of Example 1 in test mice, the following values of $LD_{50}$ were obtained.

| $LD_{50}$ in mg/kg |
| --- |
| 1700 subcutaneously |
| 1210 intraperitoneally |
| 890 intraveinously |

Various modifications of the huminates and the methods of the invention may be made without departing from the spirit or scope thereof and it is to be understood that the invention is intended to be limited only as defined in the appended claims.

What we claim is:

1. A modified alkali metal or ammonium huminate being made from molecules of the group consisting of

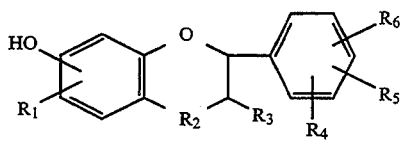

and

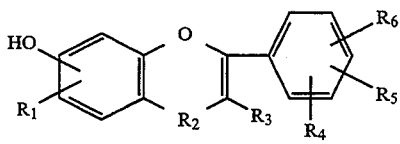

wherein $R_1$, $R_3$ and $R_4$ are individually hydrogen or —OH, $R_2$ is C=O or —CH$_2$ and $R_5$ and $R_6$ are individually selected from the group consisting of hydrogen, —OH and —OCH$_2$, with the proviso that $R_4$, $R_5$ and $R_6$ are not all hydrogen at the same time prepared by oxidizing an aqueous alkaline solution of at least one compound of the formula

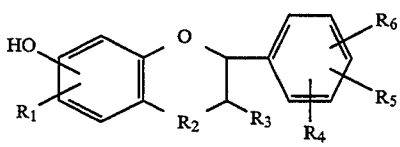

or

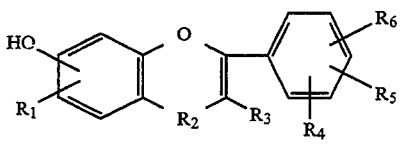

wherein $R_1$, $R_2$, $R_3$, $R_4$, $R_5$ and $R_6$ have the above definition at 15 to 40° C., then adjusting the pH to 4.5 to 7.0 and recovering the purified low molecular weight huminate.

2. An alkali metal huminate of claim 1 wherein the alkali metal is sodium.

* * * * *